United States Patent [19]
Lockwood et al.

[11] Patent Number: 5,845,254
[45] Date of Patent: Dec. 1, 1998

[54] METHOD AND APPARATUS FOR OBJECTIVELY MONITORING AND ASSESSING THE PERFORMANCE OF HEALTH-CARE PROVIDERS BASED ON THE SEVERITY OF SICKNESS EPISODES TREATED BY THE PROVIDERS

[75] Inventors: Edward J. Lockwood, Burlington; Jeffrey Tarrant; Michael Volpe, both of Hartford, all of Conn.

[73] Assignee: Cigna Health Corporation, Bloomfield, Conn.

[21] Appl. No.: 658,991

[22] Filed: Jun. 4, 1996

Related U.S. Application Data

[63] Continuation-in-part of Ser. No. 487,462, Jun. 7, 1995, Pat. No. 5,706,441.

[51] Int. Cl.$^6$ .......................... G06F 159/00; G06F 17/00
[52] U.S. Cl. ........................................ 705/2; 705/3; 705/4
[58] Field of Search ........................................ 705/2, 3, 4

[56] References Cited

U.S. PATENT DOCUMENTS

| | | | |
|---|---|---|---|
| 5,365,425 | 11/1994 | Torma et al. | 705/2 |
| 5,508,912 | 4/1996 | Schneiderman | 705/3 |
| 5,544,044 | 8/1996 | Leatherman | 705/3 |
| 5,557,514 | 9/1996 | Seare et al. | 705/2 |
| 5,724,379 | 3/1998 | Perkins et al. | 705/2 |

OTHER PUBLICATIONS

Horn, Susan D. "Measuring Severity: How Sick is Sick? How Well is Well?" Healthcare Financial Management, Oct. 1996, pp. 21–31.

Primary Examiner—Allen R. MacDonald
Assistant Examiner—Jason W. Rhodes
Attorney, Agent, or Firm—Reed Smith Shaw & McClay LLP

[57] ABSTRACT

A method and apparatus for objectively monitoring the performance of a group of health-care providers. In-patient payment claim records representative of in-patient health-care services performed for patients by health-care providers within the group of health-care providers and out-patient payment claim records representative of out-patient health-care services performed for patients by health-care providers within group of health-care providers are stored in databases. A plurality of sickness episode data records are built from the in-patient payment claim records and the out-patient payment claim records, and an objective severity adjustment analysis is performed on the sickness episode data records to form a plurality of severity-adjusted sickness episode data records. A cost-efficiency performance level is determined for each individual health-care provider within the group of health-care providers from the plurality of severity-adjusted sickness episode data records, and a qualitative performance level is determined for the group of health-care providers as a whole.

28 Claims, 12 Drawing Sheets

METHOD AND APPARATUS FOR OBJECTIVELY MONITORING AND ASSESSING THE PERFORMANCE OF HEALTH-CARE PROVIDERS BASED ON THE SEVERITY OF SICKNESS EPISODES TREATED BY THE PROVIDERS

CROSS-REFERENCES TO RELATED APPLICATIONS

This is a continuation-in-part of application Ser. No. 08/487,462, filed Jun. 7, 1995, now U.S. Pat. No. 5,706,441.

FIELD OF THE INVENTION

The present invention relates generally to systems for monitoring the activities of health-care providers. More particularly, the present invention relates to systems for assessing the relative complexity of case loads handled by individual health-care providers within a group of health-care providers. Still more particularly, the present invention relates to systems for objectively assessing the appropriateness of costs charged by different health-care providers for treating case loads of varying complexities. In addition, the present invention relates to systems for monitoring and assessing the qualitative performance of health-care providers within a group of health-care providers.

BACKGROUND OF THE INVENTION

As the cost of health-care continues to rise, increasing numbers of individuals are relying on health-care networks for delivery of health-care services. Typically, a health-care network is made up of a group of health-care providers who contract with a health-care insurer to deliver health-care services to individuals covered by the network. The health-care providers in the network typically include primary-care physicians, specialists, ancillary service providers and hospitals. The covered individuals often subscribe to the network through employers who contract directly the health-care insurer.

In order to efficiently oversee the operation of a health-care network, it is desirable for a health-care administrator to be able to monitor not only the cost of health-care services delivered by each health-care provider in the network, but also the complexity and quality of care delivered and the quality of the results achieved by each health-care provider in the network. For example, a health-care administrator overseeing a network might monitor this type of performance information in order to identify health-care providers in the network that are either overcharging for health-care services, or who may be providing sub-standard care to individuals covered by the network.

At present, the data provided to health-care network administrators from health-care providers in networks relates almost exclusively to the payment of claims. Thus, for example, when a primary care physician has an office visit with an individual covered by the network, the primary care physician will submit a claim record to the network administrator requesting payment for the office visit. The primary goal of the information contained in the claim record is to verify that the event for which payment is sought, e.g., an office visit, is covered by the network health plan. Thus, claim records submitted by individual health-care providers in the network often will not contain a complete picture of a patient's symptoms, all diagnosis that may have been made, all treatments that may have been given and/or the results of all such treatments.

Moreover, it is not uncommon for multiple claim records to be submitted by multiple health-care providers in the network for a single patient sickness event. For example, a patient having an ulcer might first be seen by a primary-care physician, then by a specialist, and ultimately be admitted to a hospital for in-patient treatment. In this situation, separate payment claim records would typically be submitted by the primary-care physician, the specialist and the hospital. Each of these claim records will typically relate only to work performed by the health-care provider submitting the claim, and will contain data limited to that which is necessary for payment of the claim.

Two different types of claim records have evolved over time in order to facilitate the payment of claims submitted by health-care providers. In particular, claims submitted by health-care providers in the network are typically categorized as either in-patient claims, or out-patient claims. In-patient claims relate to health-care services that have been delivered to an individual who has stayed overnight in the hospital, while out-patient claims relate to health-care services that have been delivered to an individual who has not required a hospital bed day. Thus, there has historically been a clear line delineating claim records pertaining to health-care services delivered to a patient within the overnight hospital environment, and those delivered to a patient outside this environment. This dividing line between services delivered inside and outside the hospital environment exists despite the fact that a single sickness event such as, for example, the ulcer sickness event described above, may typically call for health-care services to be delivered both inside and outside the hospital.

As a result of the historic differentiation between in-patient and out-patient claims, certain standard benchmarks have evolved for evaluating and monitoring the costs of particular claims. These standard benchmarks pertain almost exclusively to in-patient claims, and typically set forth a reasonable cost range that is acceptable for a given in-patient procedure or service. In the past, when a health-care provider in a network submitted a claim for doing a procedure such as, for example, an open-heart surgery, the charge submitted by the provider was compared against the standard benchmark and, if the submitted charge was within the benchmark range, it was paid by the network. In cases where the charges submitted by a health-care provider exceeded the benchmark range, only the portion of the charges within the benchmark range would be paid by the network and the remainder of the claim would be rejected for payment.

The standard benchmarks used in the past typically assumed a median complexity level for each in-patient procedure or service performed by a health-care provider. Thus, there may be a standard benchmark for evaluating the cost of an open-heart surgery procedure regardless of whether a patient has numerous complications (e.g., diabetic, asthmatic, etc.), is mildly complicated, or is otherwise healthy. Use of a standard benchmark for evaluating the costs of all open-heart surgery procedures performed by hospitals within the network may therefore inaccurately portray the cost-efficiency of various hospitals in the network. For example, it may be that certain hospitals in the network routinely handle more complicated open-heart procedures and, even though the costs of these procedures exceed the standard benchmark, the costs are justified in view of the complicated nature of the procedures. Conversely, it may be that certain hospitals in the network routinely handle the least complicated open-heart procedures and, even though the costs of these procedures normally falls below the standard benchmark, the costs are still excessive in view of their uncomplicated nature.

In many health-care networks, certain hospitals have reputations for greater expertise in particular medical areas than other hospitals in the network. For example, it may be that a given health-care network includes a university teaching hospital that is known for its cardiac care capabilities, and a suburban hospital that is known for burn treatment. Although the suburban hospital has a cardiac care department, individuals having more serious and complicated cardiac ailments tend to be treated at the university hospital. Similarly, although the university hospital has a burn treatment department, the more complicated burn cases tend to receive their care at the suburban hospital. In this situation, it would be inappropriate to apply the same standard payment benchmarks for cardiac care and burn treatment to both the university hospital and the suburban hospital. In fact, if the same standard payment benchmarks were applied to both hospitals, it would likely result in the university hospital being routinely under-compensated for its cardiac work and routinely overcompensated for its burn treatment work. Similarly, application of the same standard benchmarks at both hospitals would likely result in the suburban hospital being routinely under-compensated for its burn treatment work and routinely overcompensated for its cardiac work.

One reason that individuals choose to subscribe to a particular health-care network is the superior reputations for quality and expertise that certain hospitals in the network may have in different areas of medicine. In order to maintain the quality of services and expertise at these hospitals, it is important that each hospital be fully and appropriately compensated for all health-care services that are delivered. Otherwise, if the university hospital was routinely under-compensated for its cardiac work and the suburban hospital was routinely under-compensated for its burn work, these hospitals might lose the financial ability to continue delivering superior health-care services in their respective areas of expertise. If this were to occur, it would be undesirable both for the individuals covered by the network who may no longer have access to superior cardiac and burn care, but also for the entity running the network which may lose the ability to attract new subscribers or retain old subscribers within the network.

In order to fully and appropriately compensate each health-care provider in the network for its services, it is therefore crucial to have a mechanism for objectively measuring the complexity of the cases handled by each provider in the network. Without such information, an administrator overseeing a network has no way of differentiating between the university and suburban hospitals described in the example above. More particularly, the network administrator has no way of identifying that the university hospital is in fact handling the more complicated cardiac cases and that the suburban hospital is handling the more complicated burn cases. Although in the past network administrators may have believed that certain hospitals in the network were handling more complex cases in certain areas, the network administrators have lacked a satisfactory mechanism for objectively quantifying the relative complexity levels of matters handled by different health-care providers in the network. As a result, network administrators have lacked an effective mechanism for adjusting the compensation paid to each health-care provider in the network based on the complexity of the cases handled by each such provider.

Before an objective judgment can be made regarding the complexity of a case that has been handled by a health-care provider, it is important to know as much information as possible about the patient that was treated. For example, in order to properly assess the complexity of an open-heart surgery procedure, it will often be important to know what treatments the patient received before being admitted to the hospital, and what treatments were given after the patient was discharged from the hospital. Thus, there may be information that is necessary for assessing the complexity of the open-heart procedure which is not set forth in the hospital or in-patient claim records, but which may be found for example in out-patient claim records submitted by the patient's primary care physician for work done before and after the patient's hospital stay.

In addition to having a system for monitoring and assessing the case load complexity levels handled by each health-care provider in the network, it would be desirable for a health-care administrator overseeing a health-care network to have a comprehensive system for monitoring the performance of all individual health-care providers in the network not only from a cost point of view, but also from a quality of care point of view. Among other things, such a comprehensive system could be used for monitoring on an ongoing basis whether the health-care network as a whole is operating within budgeted limits. In cases where budgetary limits for treating certain conditions have been exceeded, the comprehensive monitoring system could be used to identify which health-care providers (if any) in the network are responsible for the budget overruns.

In addition to these budgetary functions, it would be desirable for the comprehensive monitoring system to have the ability to track the quality of care being delivered by the network as a whole in specific medical areas. For example, it is generally accepted that well-baby visits are beneficial both in maintaining the health of infants and in reducing overall health care costs. Thus, it would be desirable for the comprehensive monitoring system to be able to identify the percentage of infants in the network that are receiving well-baby care, so as to provide an objective measurement of the quality of health-care being delivered to infants in the network. Other objective measurements that would be useful for monitoring the quality of health-care delivered to patients by the network as a whole might include, for example, the percentage of diabetic patients in the health-care network receiving annual eye examinations and the percentage of female patients in the network receiving annual mammograms. It would be useful if such a system for objectively monitoring the quality of care being delivered by the network was coupled to the budget monitoring system described above, so that a network administrator could quickly and easily assess whether budgetary overruns are due to failures by the network's providers to provide the requisite quality of care level to patients in the network.

It is therefore an object of the present invention to provide a health-care monitoring system that can assess the severity of each individual sickness event experienced by individuals covered by the health-care network.

It is a further object of the present invention to provide a health-care monitoring system that can determine multiple benchmarks for evaluating the cost-effectiveness of a given procedure delivered by health-care providers within the health-care network, the multiple benchmarks corresponding to cases having different severity and complication levels.

It is a still further object of the present invention to provide a system for objectively assessing the complexity level of health-care services delivered by each health-care provider within a group of health-care providers.

It is a still further object of the present invention to provide a health-care monitoring system that is based on the tracking and assessment of individual sickness events irrespective of whether such sickness events involve in-patient services, out-patient services, or both.

It is yet a further object of the present invention to provide a system for objectively assessing the cost-efficiency of each health-care provider within a network on an illness-by-illness basis, wherein the cost-efficiency assessment for each health-care provider is based not only on the cost of the health-care services delivered by the provider, but also on the complexity and severity of the cases treated by the provider.

It is yet a further object of the present invention to provide a comprehensive health-care monitoring system that may be used by an administrator overseeing a health-care network to monitor on an ongoing basis whether the health-care network is operating within budgetary limits, and for objectively assessing the complexity levels of case loads handled by individual health-care providers and the quality of care delivered by all the health-care providers in the network when budgetary limits have been exceeded.

These and still other objects of the invention will become apparent upon study of the accompanying drawings and description of the invention.

SUMMARY OF THE INVENTION

The present invention is directed to a method and apparatus for objectively monitoring the performance of a group of health-care providers. In-patient payment claim records representative of in-patient health-care services performed for patients by health-care providers within the group of health-care providers and out-patient payment claim records representative of out-patient health-care services performed for patients by health-care providers within group of health-care providers are stored in databases. A plurality of sickness episode data records are built from the in-patient payment claim records and the out-patient payment claim records, and an objective severity adjustment analysis is performed on the sickness episode data records to form a plurality of severity-adjusted sickness episode data records. A cost-efficiency performance level is determined for each individual health-care provider within the group of health-care providers from the plurality of severity-adjusted sickness episode data records, and a qualitative performance level is determined for the group of health-care providers as a whole.

DETAILED DESCRIPTION OF THE PREFERRED EMBODIMENT

Figure 1:
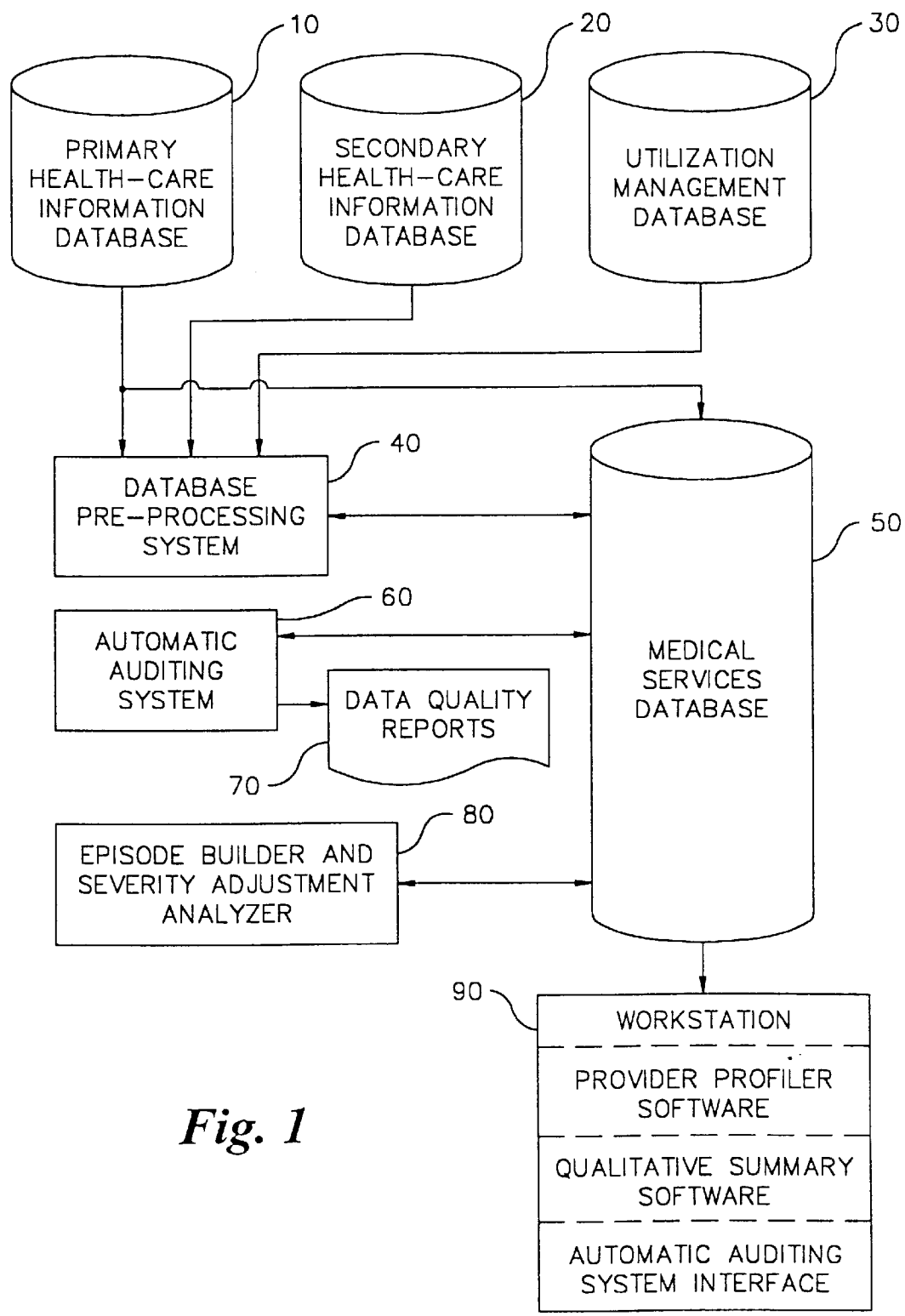
FIG. 1 is a block diagram showing the operation of a system for objectively monitoring and assessing the performance of a group of health-care providers in accordance with a preferred embodiment of the present invention.

Referring now to FIG. 1, there is shown a block diagram illustrating the operation of a system 100 for objectively monitoring and assessing a group of health-care providers in accordance with a preferred embodiment of the present invention. System 100 is formed of primary health-care information database 10, secondary health-care information database 20, and a utilization management database 30. Records stored in databases 10, 20 and 30 are transmitted in the form of digital signals to database pre-processing system 40, where the records are linked and matched together. The linked and matched records are then transmitted in the form of digital signals to medical services database 50 for storage. Records stored in medical services database 50 are next transmitted in the form of digital signals to a data processing system 80, which builds a plurality of sickness episode data records by combining information from records stored in database 50. Each sickness episode data record corresponds to an individual sickness episode for which health-care services were performed for a patient by one or more health-care providers. Data processing system 80 also performs an objective severity assessment for each sickness episode data record. In response to each objective severity assessment, data processing system 80 assigns an episode severity score to each of the sickness episode data records. The episode severity scores, together with other information stored in the claim records in database 50, are transmitted in the form of digital signals to a workstation 90. In addition to performing other functions, workstation 90 receives these digital signals from database 50, and determines a case load complexity level for each health-care provider within the group of health-care providers from the severity scores. Each case load complexity level determined by workstation 90 is representative of a patient case load serviced by a particular health-care provider within the group of health-care providers.

Figure 2:
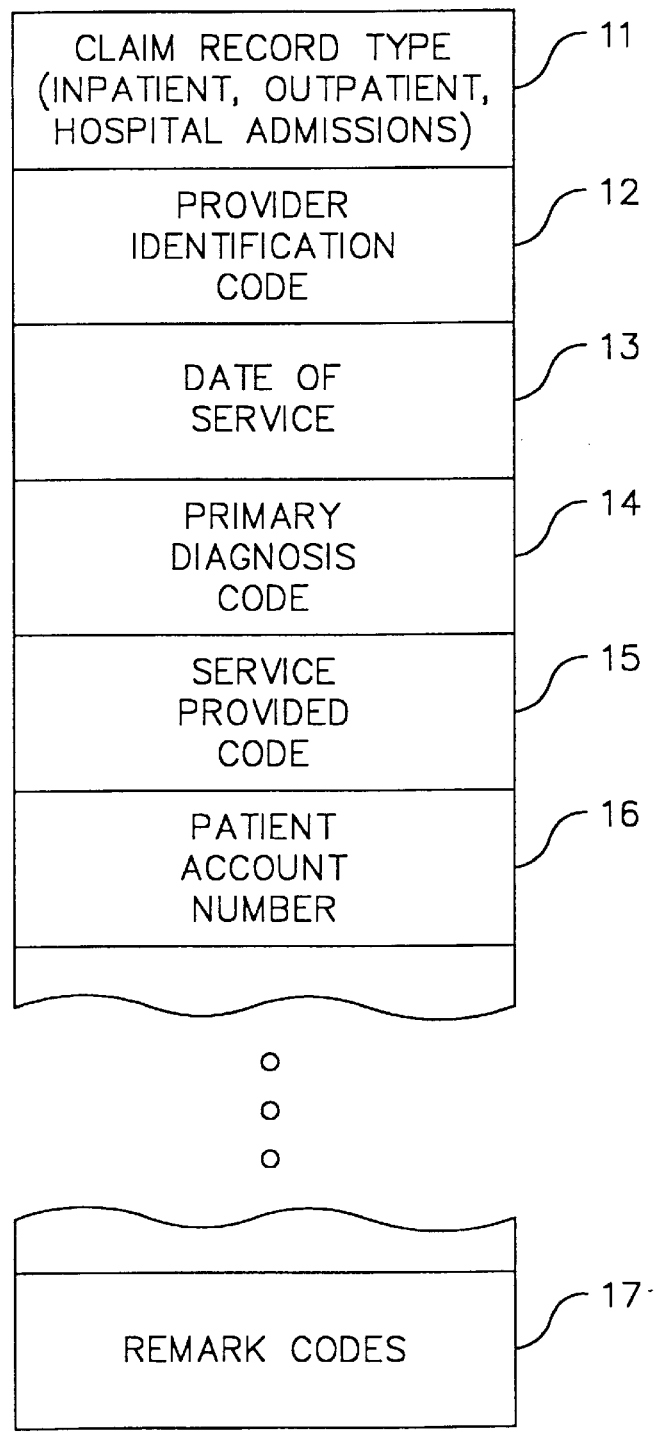
FIG. 2 is a diagram showing the data structure of a claim payment record stored in a primary health-care database in accordance with a preferred embodiment of the present invention.

Referring now to FIG. 2, there is shown a diagram illustrating the data structure format of an exemplary claim payment record stored in primary health-care database 10 in accordance with a preferred embodiment of the present invention. Each claim record stored in primary health-care database 10 represents a request for payment by a health-care provider for an individual service or procedure performed by the health-care provider for one of the patients in the network. The primary purpose of the information contained in the claim records stored in database 10 is to verify that the service or procedure for which payment is sought, e.g., an office visit, is covered by the network health plan. Since the claim records stored in database 10 relate primarily to claim payment, these claim records will not typically contain a complete picture of a patient's symptoms, all diagnoses that may have been made by the health-care provider submitting the claim record, all treatments that may have been given by the provider submitting the claim record and/or the results of all such treatments.

The claim records stored in primary health-care information database 10 fall into the two claim record categories that have been used historically by health plan administrators for processing claims for payment. Thus, the claims submitted by health-care providers in the network are typically stored in database 10 as either in-patient claim records or out-patient claim records. Each in-patient claim record relates to an individual health-care service or procedure that was performed for a hospitalized patient covered by the network, while each out-patient claim record relates to an individual health-care service or procedure that was performed for a covered patient outside of a hospital. Since a single sickness event such as, for example, arteriosclerosis, may require multiple health-care services and procedures both inside (e.g., angioplasty, bypass surgery) and outside the hospital (e.g., out-patient office visits to primary care physician and cardiologist) from more than one health care provider, multiple different claim records pertaining to a single sickness event (or episode) will typically be stored simultaneously in database 10.

Referring still to FIG. 2, an exemplary data record stored in primary health-care database 10 includes a claim record type field 11 for identifying the type of claim (i.e., in-patient or out-patient) stored in the data record. A provider identification field 12 contains an alphanumeric code representing the health-care provider in the network submitting the claim for payment. A unique health-care provider identification code is used to represent each health-care provider in the network. Each data record stored in database 10 also includes a date-of-service field 13 representing the date on which the health-care provider submitting the claim performed the procedure or service that is the subject of the request for payment. A primary diagnosis code field 14 in the data record contains a code representing a primary diagnosis of a patient's condition that may have been made by the health-care provider submitting the claim. As explained more fully below, a health-care provider may make multiple diagnoses during treatment of an individual patient. However, since only the primary diagnosis is used in processing a claim for payment, only the primary diagnosis is typically stored as part of a claim record in primary database 10. The data record further includes a service provided code field 15 containing a code representing the service or procedure that the health-care provider performed and for which payment is being requested. Field 15 will contain codes representing such things as routine primary care physician office visits, office visits with specialists, specific surgical procedures, specific diagnostic procedures, etc. A patient account number field 16 in the data record contains a code representing the covered individual for whom the health-care provider performed the service or procedure identified in field 15. The code in the patient account number field 16 may also contain information representing the entity paying the premium for the covered individual such as, for example, the covered individual's employer. Finally, each data record stored in database 10 will preferably include a remark code field 17 that the network administer may use for storing payment processing information. The remark code field 17 may be used, for example, to store a code indicating that the administrator declined to pay the claim to health-care provider because the individual identified in field 16 had a policy with a deductible amount that had not yet been met.

Although FIG. 2 shows a specific data structure format having specific fields ordered in a particular sequence, it will be understood by those skilled in the art that other data structure formats with different fields ordered in other sequences may be used for storing data records in primary health-care database 10.

Figure 3:
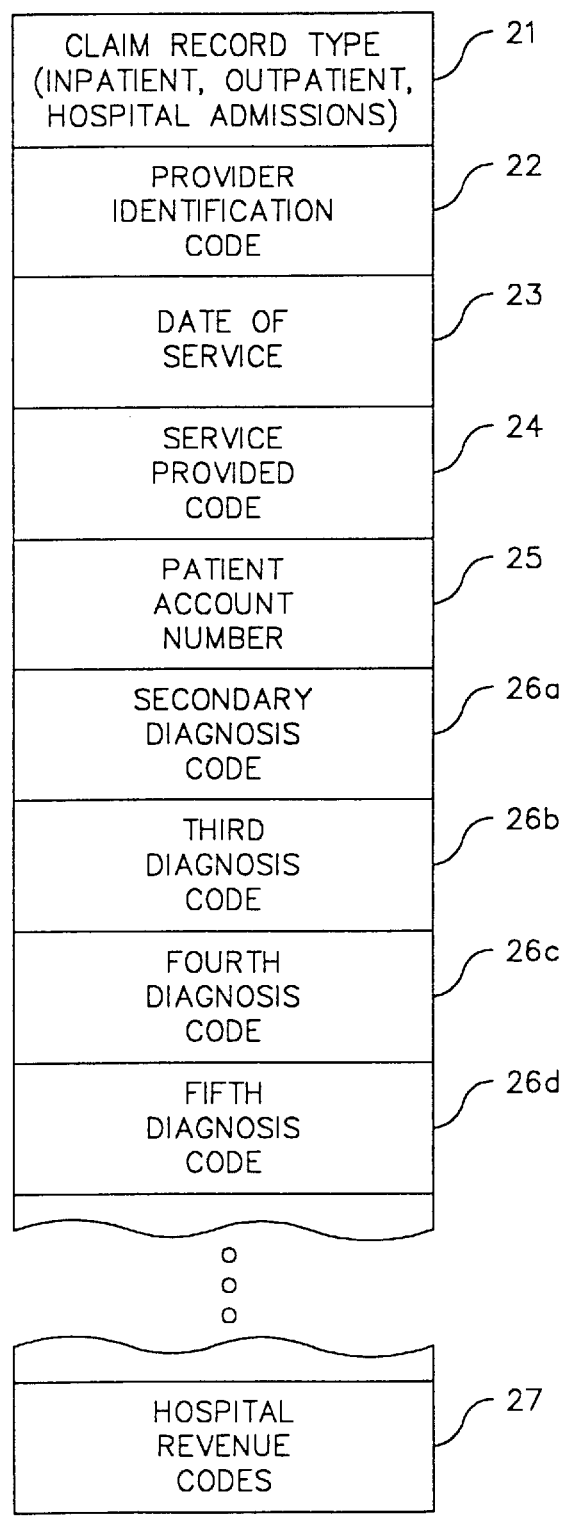
FIG. 3 is a diagram showing the data structure of a claim record stored in a secondary health-care database in accordance with a preferred embodiment of the present invention.

Referring now to FIG. 3, there is shown a diagram illustrating the data structure of a claim record stored in secondary health-care database 20 in accordance with a preferred embodiment of the present invention. Although only information necessary for payment of a claim is typically stored in primary database 10, it is common that health-care providers submitting claims for payment will also include supplemental information in their claim submission forms which does not correspond to a data record field stored in primary health-care database 10. In the past, since this supplemental information was not required to process the claim for payment, the supplemental information was typically discarded after the claim record in primary database 10 was in place. In the present invention, such supplemental information is retained in a supplemental data record stored in secondary health-care information database 20.

Referring still to FIG. 3, an exemplary data record stored in secondary health-care database 20 includes a claim record type field 21 for identifying the type of claim associated with the data record; a provider identification field 22 containing an alphanumeric code representing the health-care provider in the network associated with the claim; a date-of-service field 23 representing the date of service associated with the claim; a service provided code field 24 containing a code representing the service or procedure that the health-care provider performed; and a patient account number field 25. Fields 21, 22, 23, 24 and 25 correspond substantially to fields 11, 12, 13, 15 and 16 discussed more fully above. The data records stored in database 20 also include a secondary diagnosis code field 26a, a tertiary diagnosis code field 26b, a fourth diagnosis code field 26c and a fifth diagnosis code field 26d. As mentioned above, although a health-care provider submitting a claim may make multiple diagnoses during treatment of an individual patient, only the primary diagnosis is used for processing the claim for payment. All diagnoses other than the primary diagnosis are saved by the present invention and stored in the form of codes in fields 26a–d. Each data record stored in database 20 also includes a hospital revenue code field 27 which is used to identify an entity within a hospital that performed a service or procedure for which payment is being requested. By way of example, field 27 may be used to indicate whether a patient received care in a regular care room or an intensive care unit.

Although FIG. 3 shows a specific data structure format having specific fields ordered in a particular sequence, it will be understood by those skilled in the art that other data structure formats with different fields ordered in other sequences may be used for storing data records in secondary health-care database 20.

Figure 4:
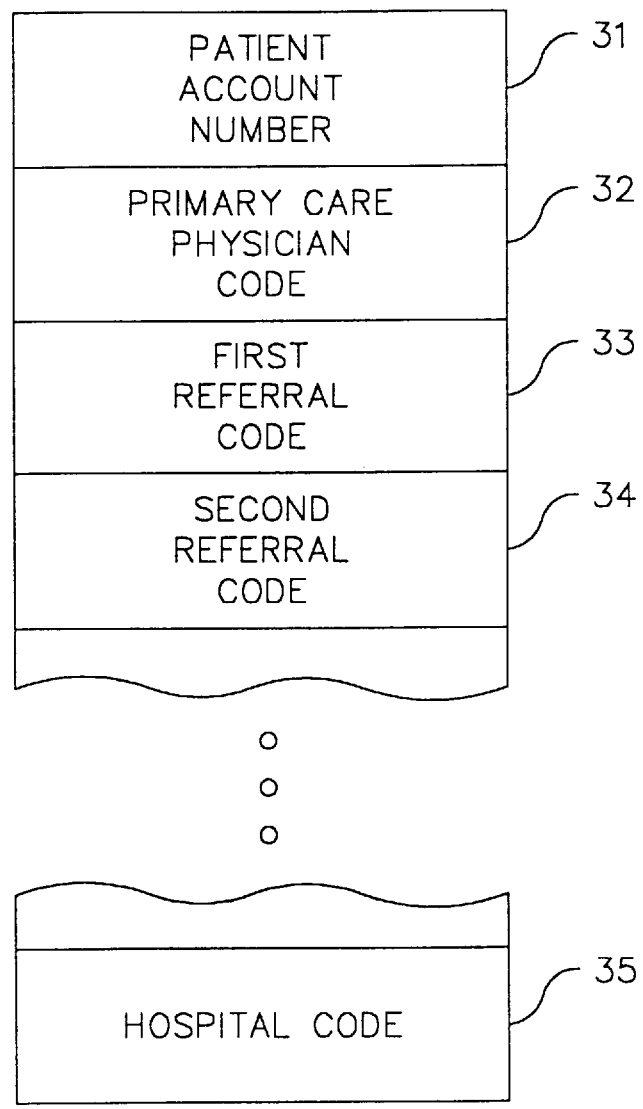
FIG. 4 is a diagram showing the data structure of a patient referral record stored in a utilization management database in accordance with a preferred embodiment of the present invention.

Referring now to FIG. 4, there is shown a diagram illustrating the data structure of a patient referral record stored in utilization management database 30 in accordance with a preferred embodiment of the present invention. The purpose of each referral record stored in database 30 is to maintain an audit trail of referrals initiated by each primary care physician in the network. Each data record stored in database 30 contains a patient account number field 31 containing a code representing the identity of the covered individual that is the subject of the audit trail. A primary care physician code field 32 is provided for storing a code representing the primary care physician who initially referred the patient identified in field 31 to a further health-care provider. A code corresponding to the identity of the health-care provider that received the initial referral from the primary care physician is stored in field 33. In the event the provider identified in field 33 found it necessary to refer the patient to a further health-care provider or to a hospital, a code representing the provider receiving the further referral would be stored in fields 34 or 35, respectively. Although FIG. 4 shows a specific data structure format having specific fields ordered in a particular sequence, it will be understood by those skilled in the art that other data structure formats with different fields ordered in other sequences may be used for storing data records in utilization management database 40.

Figure 5:
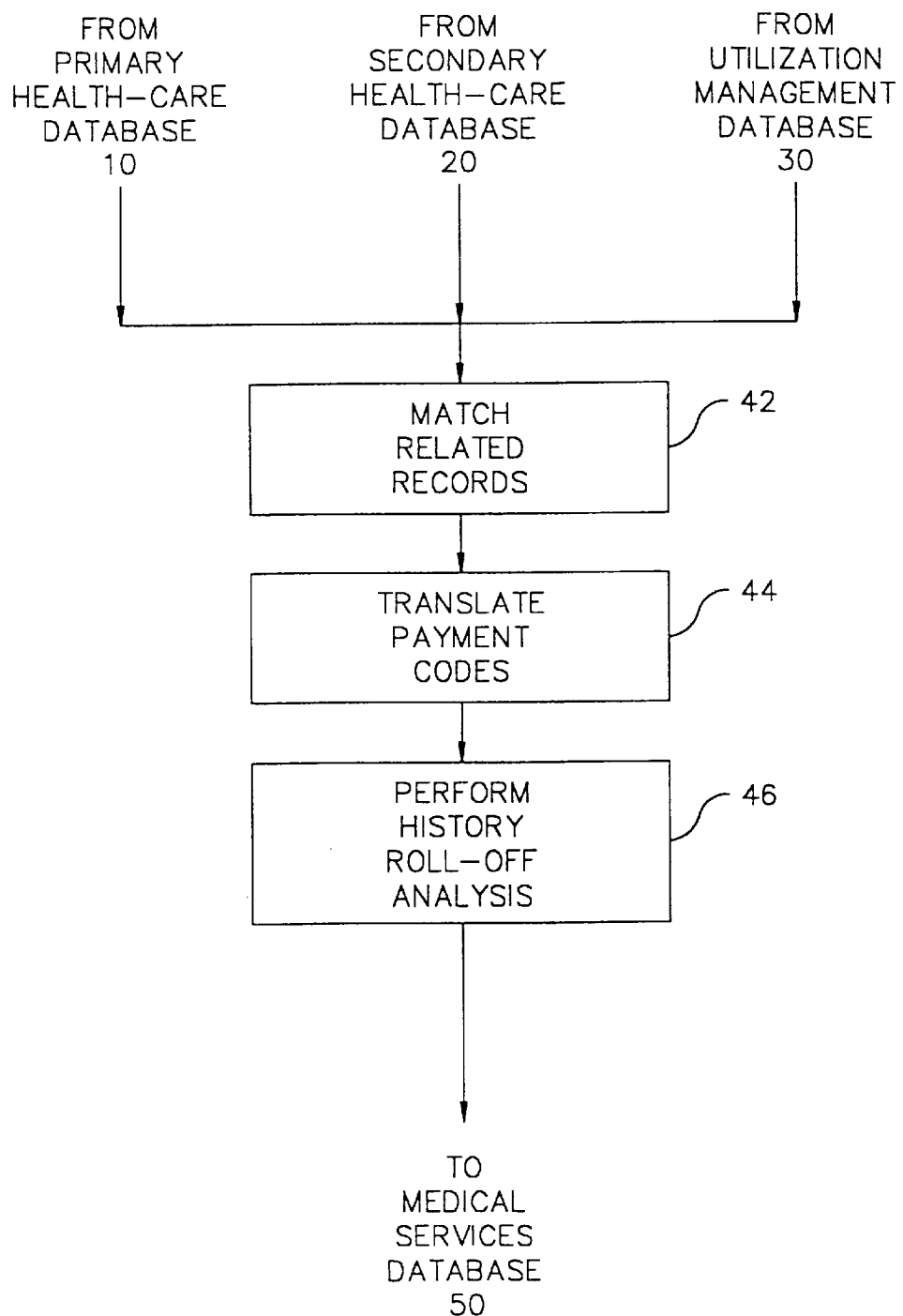
FIG. 5 is a flow diagram showing the operation of a database pre-processing system in accordance with a preferred embodiment of the present invention.

Referring now to FIG. 5, there is shown a flow diagram illustrating the operation of a database pre-processing system 40 in accordance with a preferred embodiment of the present invention. Database pre-processing system 40 preferably receives digital signals from databases 10, 20 and 30 representative of the records stored in these databases, processes these signals, and then transmits digital signals representative of records that have been linked and matched in accordance with the process of FIG. 5 to medical services database 50. The purpose of data pre-processing system 40 is to link together related records stored in databases 10, 20 and 30 prior to the storage of such records in medical services database 50. For purposes of database pre-processing system 40, two or more data records are considered related if they pertain to the same sickness event experienced by an individual covered by the network. Thus, for example, if an individual covered by the network had a sickness event such as an ulcer, and the covered individual saw a primary care physician, then a specialist, and was ultimately admitted to a hospital for treatment, the following related data records would likely exist for this sickness event in databases 10, 20 and 30: (1) three primary claim records (one for the primary care physician, one for the specialist, and one for the hospital) would be stored in primary health-care database 10, (2) three corresponding supplemental claim records would be stored in secondary health-care database 20, and (3) a data record would be stored in utilization management database 30 showing the referral path of the patient from the primary care physician, to the specialist, and ultimately to the hospital. As explained more fully below, database pre-processing system 40 scans all the records in databases 10, 20 and 30 and, based on the information contained in those records, links together each group of records that are related to the same sickness event. Database pre-processing system 40 is preferably implemented in software on a microprocessor or a general purpose digital mainframe computer.

Referring still to the flow diagram of FIG. 5, in step 42, data pre-processing system 40 matches together related data records from databases 10, 20 and 30. In step 42, data records from databases 10 and 20 are initially linked together into sub-groups of data records sharing the same patient identification code, health-care provider code, and date-of-service code. Thereafter, the records from database 30 are scanned to determine if there is a referral record in database 30 associated with any of the sub-groups of records initially linked together from databases 10 and 20. Each sub-group of data records associated with the same referral record is then linked together into a group of data records. A directory containing the addresses of the data records in each record group and sub-group is formed in step 42 and stored in medical services database 50.

In step 44, following the linking of the data records into groups and sub-groups, the codes stored in fields 15 and 24 are translated from codes representing generic events or procedures to codes representing more specific events or procedures. For example, when a patient with stomach pains sees his primary care physician for an office visit, a payment code representative of a standard office visit will initially be stored in field 15. Using information from data records in the same group or sub-group as the record containing field 15, a new more specific payment code will be substituted for the standard office visit code. The substituted code will represent, for example, that the patient had an office visit with his primary care physician to address a gastrointestinal problem. Among other things, the diagnosis codes stored in related data records are used to translate generic payment codes into more specific codes in step 44.

In step 46, following the translation of the payment codes, the record groups and sub-groups previously linked together are subjected to a "history rolloff" analysis. In the preferred embodiment of the present invention, each group or sub-group of data records linked together in step 42 will span a time frame no greater than 24 months. Thus, if there are related records going back further than 24 months, such records will typically be excluded from the groups and sub-groups that are linked together in step 42. In step 46, a "history rolloff" analysis is performed prior to excluding records going back further than 24 months. The purpose of the history rolloff analysis is to determine whether there is any information in the data records preceding the beginning of the 24 month window that relates to data records with service dates falling within the 24 month window. If, for a given record group or sub-group, records preceding the beginning of the 24 month window are found to relate to data records falling within the 24 month window, then the 24 month window cutoff is not applied to the record group or sub-group in step 46.

Figure 6:
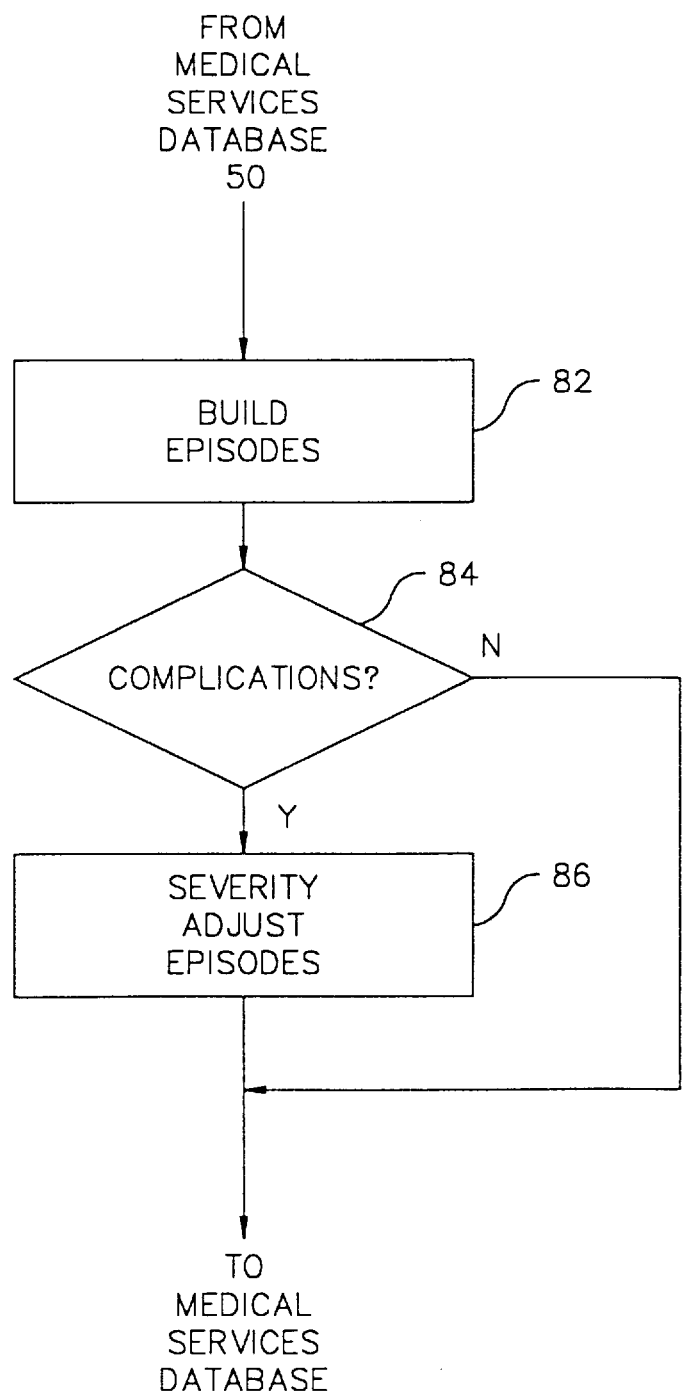
FIG. 6 is a flow diagram showing the operation of an episode builder and severity adjustment analysis system in accordance with a preferred embodiment of the present invention.

Referring now to FIG. 6, there is shown a flow diagram showing the operation of an episode builder and severity adjustment analysis system 80 in accordance with a preferred embodiment of the present invention. Episode builder 80 preferably receives digital signals from database 50 representative of records stored in the database, processes these signals, and then transmits digital signals representative of episodes built and episode severity scores determined in accordance with the process of FIG. 6 to medical services database 50.

In step 82, system 80 uses the data record groups and sub-groups formed by system 40 to build a plurality of sickness episode data records. Each sickness episode data record built by system 80 corresponds to an individual "sickness episode" during which health-care services were performed for a patient by at least one health-care provider from the health-care network. In the preferred embodiment, the term "sickness episode" corresponds to a time period that begins when a patient is injured or begins to feel sick and ends when the patient is no longer sick or injured. Since a patient may begin to feel sick prior to seeing a health-care provider from the network, a sickness episode may begin before any health-care services are provided for the patient by any health-care provider in the network. In addition, since a patient may see several health-care providers in the network during a single sickness episode, a typical sickness episode data record may include information about both in-patient and out-patient services that were provided to the patient during the episode.

Among other things, each sickness episode data record built by system 80 will contain data representative of all diagnoses pertaining to the sickness episode, and all procedures and services performed by each health-care provider in the network in connection with the sickness episode. The diagnoses included in each sickness episode data record will include all diagnoses rendered by the health-care providers that were involved in the sickness episode, regardless of whether such diagnoses were rendered in connection with in-patient or out-patient services. Similarly, since a typical sickness episode may call for both in-patient and out-patient services, a sickness episode data record may contain data representing both in-patient and out-patient services and procedures that were performed for a patient during the episode.

Following the building of sickness episode data records in step 82, each sickness episode data record is analyzed in step 84 to determine whether the sickness episode embodied by the episode data record should be classified as routine or complicated. In one embodiment, the services and procedure codes stored in the episode data record are compared against a predetermined list of out-of-the-ordinary procedures. In the event any out-of-ordinary procedures were performed during the episode, the episode will be classified as complicated; otherwise the episode will be classified as routine. In an alternate embodiment of the present invention, the primary diagnoses and all other diagnoses stored in the sickness episode data record may be used to determine whether the sickness episode was routine or complicated. In particular, in step 84, the primary diagnosis associated with the episode may be used to retrieve a predetermined list of supplementary diagnoses that may be associated with the primary diagnosis. If there is a match between any of the supplemental diagnoses stored in the sickness episode data record and those stored on the retrieved list, the episode data record will be classified as complicated; otherwise, the episode data record will be classified as routine.

In step 86, each sickness episode data record that was classified as complicated is subjected to a severity adjustment analysis. The purpose of the severity adjustment analysis is to objectively rank (or score) the complexity of the sickness episode embodied in the data record. In the preferred embodiment, the severity adjustment analysis uses information from the diagnoses and procedures stored in the sickness episode data record to assign a numerical severity score ranging from 1 (least severe) to 16 (most severe) to the sickness episode data record. After each sickness episode data record that was classified as complicated has been subjected to a severity adjustment analysis in step 86, the sickness episode data records together with their assigned severity scores are stored in medical services database 50.

Episode builder and severity adjustment system 80 is preferably implemented in software on a microprocessor or a general purpose digital mainframe computer.

Figure 7:
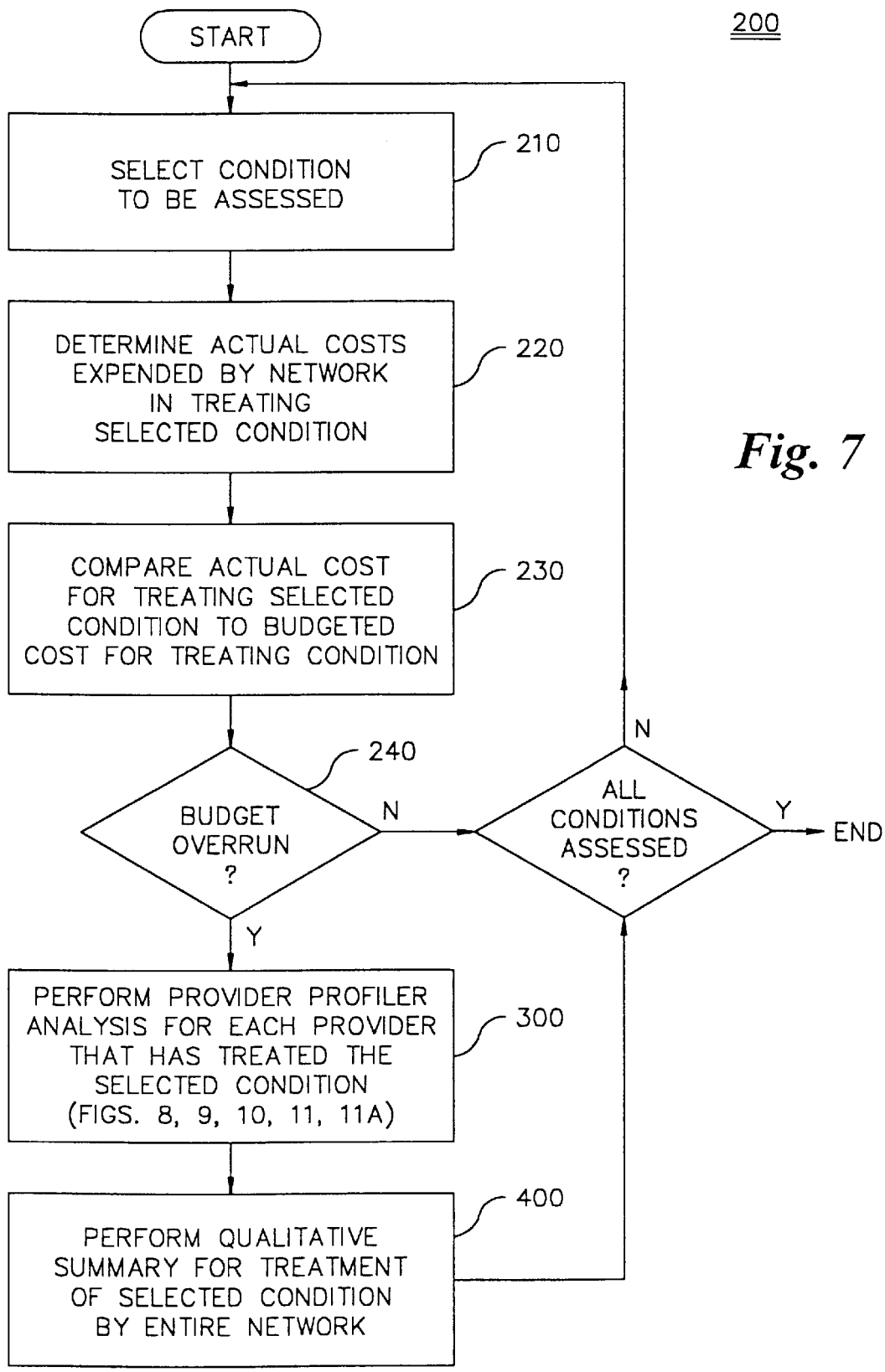
FIG. 7 is a flow diagram showing the operation of a system that is operable on a workstation for objectively monitoring and assessing the performance of a group of health-care providers in accordance with a preferred embodiment of the present invention.

Referring now to FIG. 7, there is shown a flow diagram illustrating the operation of a system 200 for objectively monitoring and assessing the performance of a group of health-care providers in accordance with a preferred embodiment of the present invention. System 200 is preferably implemented in software on a workstation 90. By way of an overview, system 200 includes three sub-systems. The first sub-system includes steps 210–240 and is used for monitoring on an ongoing basis and at regular intervals whether the costs being expended by the network as a whole for treating various conditions are within predetermined budgetary levels, or alternatively, whether the network as a whole is having budget overruns in connection with its treatment of such conditions. The second sub-system includes provider profiler system 300 and is explained more fully in conjunction with FIGS. 8, 9, 10, 11 and 11A. The third sub-system includes qualitative performance summary system 400, which is used for objectively determining and assessing the qualitative performance level of the network as a whole in treating various conditions. In the preferred embodiment shown in FIG. 7, sub-systems 300 and 400 are used in conjunction with the budget monitoring sub-system (steps 210–240) in order to attempt to identify potential causes or reasons for budgetary overruns identified by the budget monitoring sub-system. It will be understood by those skilled in the art that sub-systems 300 and 400 may be used in a stand-alone mode, separate and apart from the budget monitoring system of steps 210–240, for performing provider profiling and determining qualitative performance levels associated with conditions and procedures other than those identified by the budget monitoring system.

Referring still to FIG. 7, in step 210 the budget monitoring sub-system selects a medical condition for cost assessment. The selected condition will correspond, for example, to a specific medical condition typically treated by health-care providers in the health-care network. In step 220, the budget monitoring sub-system determines the actual costs expended by all providers in the network in treating the selected condition. Thus, for example, if the condition selected in step 210 corresponded to severe coronary artery blockage, the actual cost figure determined in step 220 may include all costs spent by the network as a whole in performing coronary bypass surgery. In steps 230 and 240, the actual cost figure expended on the selected condition is compared against a predetermined budgeted cost amount for treating the selected condition. In one embodiment, this predetermined budget cost amount is determined by looking at amounts previously expended by the network on treating the selected condition, and then using these previous expenditure amounts as a basis for projecting what amounts should be budgeted presently for treating the selected condition. If in step 240 the budget monitoring sub-system determines that the actual cost for treating the selected condition exceeds the budgeted amount for treating the condition, then systems 300 and 400 are employed to attempt to identify the cause of the overrun. Alternatively, if no budgetary overrun is identified in step 240, then the process is repeated from step 210 for a further selected condition. In the preferred embodiment, the budget monitoring sub-system of steps 210–240 is used on a regular basis (e.g., weekly, monthly or quarterly) to evaluate each condition typically treated by providers in the network and determine whether the costs expended in treating each such conditions are within budgeted amounts.

Referring still to FIG. 7, in the event that the budget monitoring sub-system determines that there has been a budgetary overrun in connection with the selected condition, provider profiler system 300 (shown and described in connection with FIGS. 8, 9, 10, 11 and 11A) is used to identify those health-care providers in the network that have performed inefficiently from a cost standpoint in treating the selected condition. In addition, in instances where budgetary overruns are present, system 400 may be used to determine whether the quality of care being delivered in treating the selected condition is up to a predetermined standard. It is important to assess the quality of care for those conditions that involve budgetary overruns, because a sub-standard quality of care level can often result in the expenditure of excess amounts for medical costs.

Referring still to FIG. 7, qualitative performance summary system 400 is provided for objectively measuring the qualitative performance of the network as a whole in treating a selected condition. Examples of objective qualitative performance levels determined by system 400 might include the percentage of young children covered by the network that have received "well-baby" care, the percentage of diabetic patients in the network that have received annual eye exams, and the percentage of female patients in the network receiving annual mammograms. System 400 preferably determines each of these percentages by evaluating the claim records stored in databases 10, 20, 30 and 50, and then compares each such percentage to an industry standard to determine whether the quality of care being delivered by the network as a whole is up to industry standards. In instances where there has been a budgetary overrun and the quality performance percentage associated with treating the selected condition (from step 210) is below the industry standard, this fact is signalled to the network administrator through workstation 90. The administrator may then take corrective action by, for example instructing the providers in the network to schedule and perform further procedures so as to improve the quality performance percentage of the network as a whole for the selected condition.

In the preferred embodiment of the present invention, workstation 90 is also coupled through database 50 to an automatic auditing system 60 for auditing individual in-patient and out-patient claim records stored in database 50. Auditing system 60 can be accessed on workstation 90 through interface software resident on the workstation. The purpose of the automatic auditing system is to review each claim record submitted for payment by a health-care provider, and identify certain sentinel events that are evidenced by the claim records. Such sentinel events may include, for example, experimental or unwarranted medical procedures that are not approved for coverage by the network.

Figure 8:
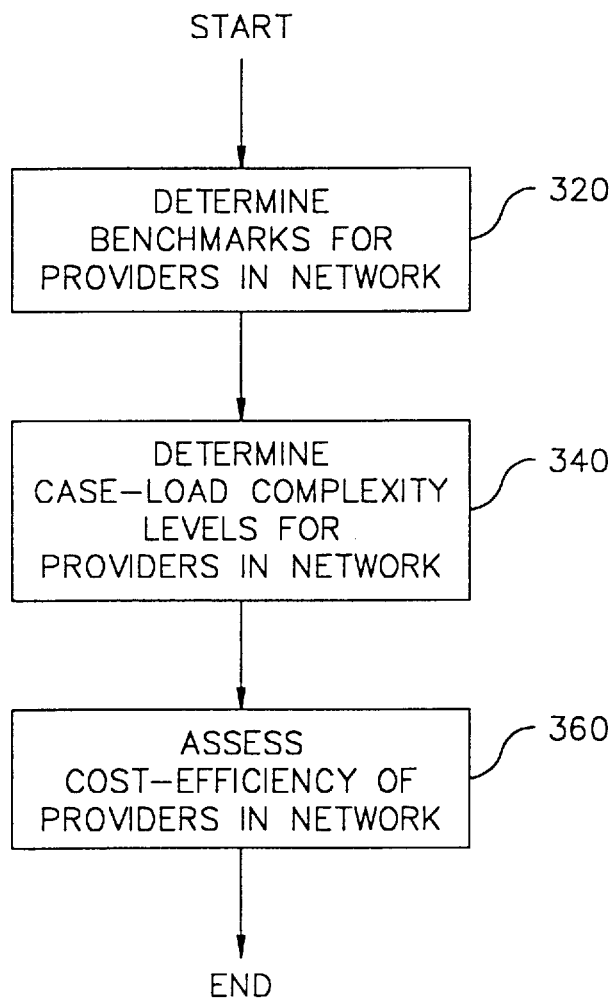
FIG. 8 is a flow diagram showing the operation of a provider profiler system for assessing the performance of individual health-care providers within a group of health-care providers in accordance with a preferred embodiment of the present invention.

Referring now to FIG. 8, there is shown a flow diagram showing the operation of a provider profiler system 300 for assessing the performance of individual health-care providers within a network of health-care providers in accordance with a preferred embodiment of the present invention. System 300 is preferably implemented in software on workstation 90. As discussed more fully below, the operation of system 300 may be broken down into three main steps, each of which is comprised of several sub-steps. In main step 320, one or more severity comparison benchmarks are determined for each common procedure that was performed by the health-care providers in the network. Next, in main step 340, case load complexity levels representing the overall severity of cases handled by a health-care provider are determined for each health-care provider in the network.

Finally, in main step 360, a cost-efficiency assessment is performed on each health-care provider in the network based on the benchmarks from step 340. As explained more fully below, the purpose of using the severity comparison benchmarks in assessing the cost-efficiency of the health-care providers is to insure that health-care providers that routinely handle more complicated cases are compared from a cost standpoint against like health-care providers that also routinely handle more complicated cases, and that health-care providers that routinely handle less complicated cases are compared from a cost standpoint against like health-care providers that also routinely handle less complicated cases. Thus, the use of the severity comparison benchmarks in the present invention insures that the exemplary university and suburban hospitals discussed in the background of this specification would never be compared against each other from a cost standpoint in assessing the cost-efficiencies of their respective cardiac and burn treatment units.

Figure 9:
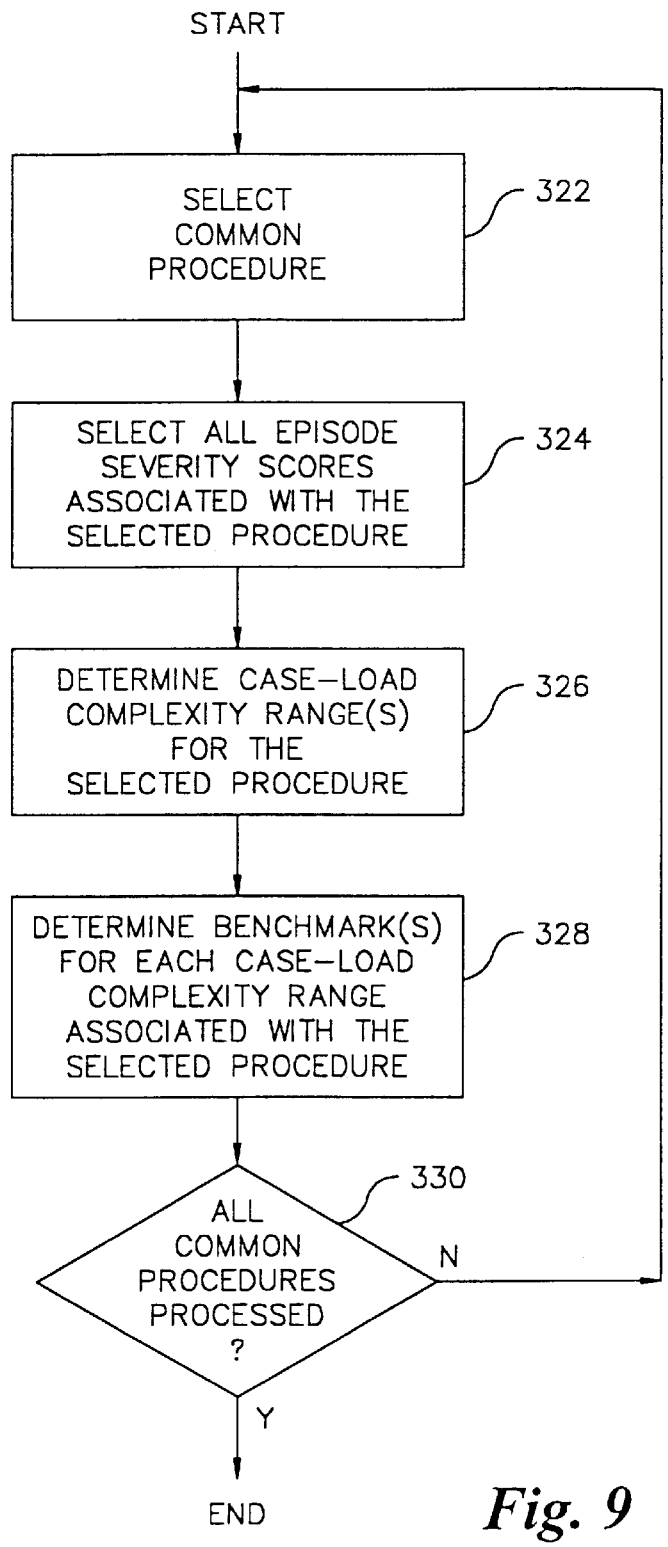
FIG. 9 is a flow diagram showing the operation of a system for determining severity comparison benchmarks that are used for assessing the relative performance of individual health-care providers within a group of health-care providers in accordance with a preferred embodiment of the present invention.

Referring now to FIG. 9, there is shown a flow diagram illustrating the operation of main step 320 and showing a system for determining severity comparison benchmarks that are used for assessing the relative performance of individual health-care providers within a group of health-care providers in accordance with a preferred embodiment of the present invention. In step 322, a common procedure or service performed by multiple health-care providers in the network for patients is selected for analysis. When subsystem 300 is used in conjunction with the budget monitoring sub-system (steps 210–240) of system 200, the common procedure or service may correspond, for example, to the procedure typically used for treating the condition selected in step 210. In step 324, each sickness episode data record in database 50 is scanned and each sickness episode data record which includes a procedure code showing that the selected common procedure was performed during the sickness episode by any health-care provider in the network is selected. In step 326, a plurality of complexity ranges are determined for the selected common procedure by analyzing the severity scores associated with the sickness episode data records selected in step 324. In one embodiment, the severity scores associated with the selected sickness episodes are arranged in ascending order and the list is then divided at its midpoint into a first group of less severe severity scores and a second group of more severe severity scores. In step 328, a severity comparison benchmark is determined for each of the complexity ranges determined in step 326. Thus, in the embodiment discussed above, a first severity comparison benchmark is determined from the first group of less severe severity scores and a second severity comparison benchmark is determined from the second group of more severe severity scores determined in step 326. The first severity comparison benchmark is preferably determined by either averaging or taking the statistical median of the first group of less severe severity scores, and the second severity comparison benchmark is preferably determined by either averaging or taking the statistical median of the second group of more severe severity scores. It will be understood by those skilled in the art that the severity scores selected in step 324 may divided into more than two complexity ranges, and that statistical techniques other than averaging or median selection may be used to determine severity comparison benchmarks from such complexity ranges. The process of determining severity comparison benchmarks may be repeated (as shown by block 330) on a procedure-by-procedure basis for each procedure or service performed by health-care providers in the network.

Figure 10:
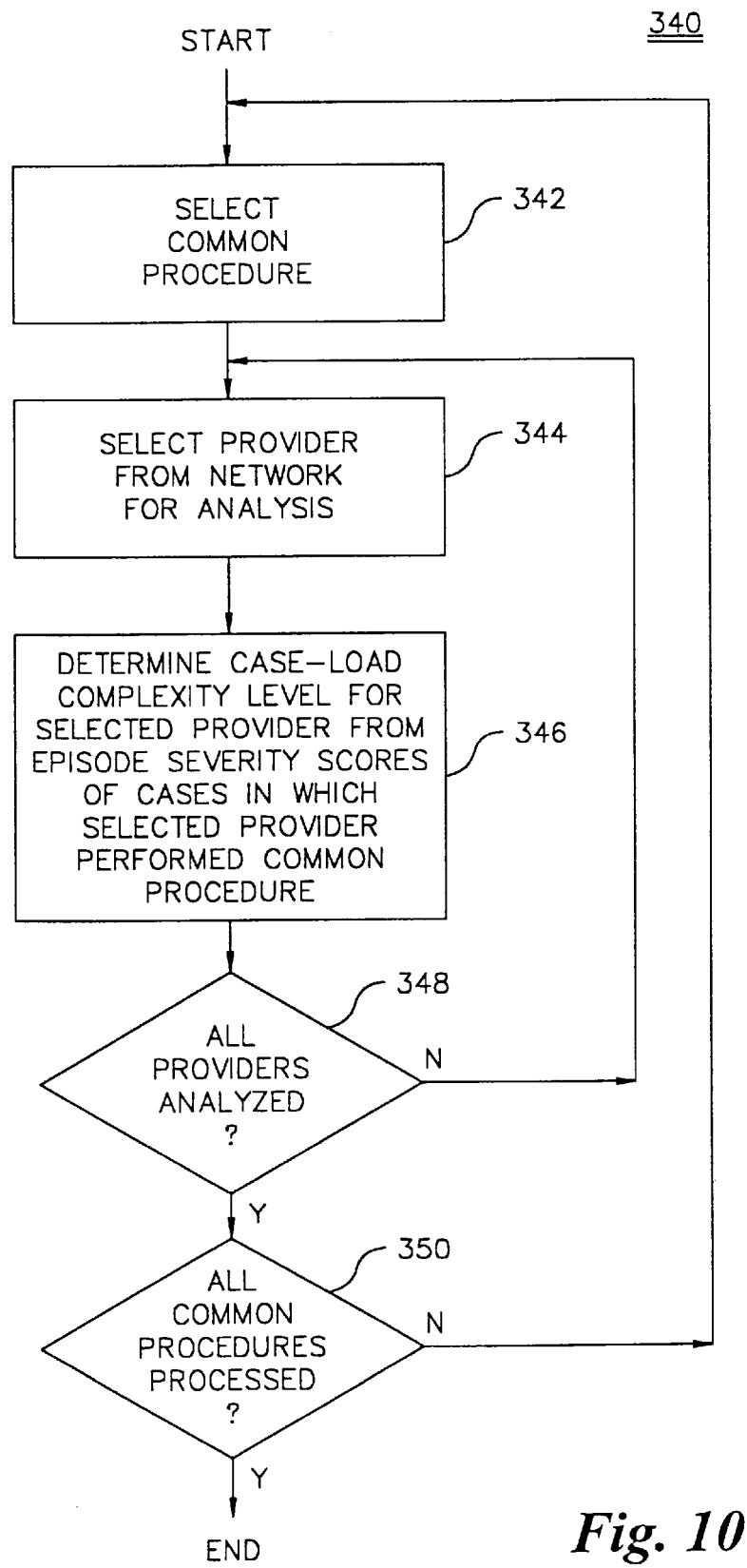
FIG. 10 is a flow diagram showing the operation of a system for determining individual case load complexity levels for individual health-care providers within a group of health-care providers in accordance with a preferred embodiment of the present invention.

Referring now to FIG. 10, there is shown a flow diagram illustrating the operation of main step 340 and showing a system for determining individual case load complexity levels for individual health-care providers within a network of health-care providers in accordance with a preferred embodiment of the present invention. In step 342, a common procedure or service performed by multiple health-care providers in the network for patients is selected for analysis. When sub-system 300 is used in conjunction with the budget monitoring sub-system (steps 210–240) of system 200, the common procedure or service may correspond, for example, to the procedure typically used for treating the condition selected in step 210. In step 344, a health-care provider from the network is selected for evaluation. In step 346, a case load complexity level associated with the selected common procedure is determined for the selected provider. In this step, all sickness episode data records are identified wherein the selected health-care provider performed the common procedure for a patient covered by the network. The severity scores assigned to the identified sickness episode data records are then either averaged or a median of these scores is taken to determine a case load complexity level associated with the selected common procedure for the selected provider. It will be understood by those skilled in the art that statistical techniques other than averaging or median selection may be used to determine a case load complexity level from associated severity scores in step 346. As shown by blocks 348 and 350, the process of determining case load complexity levels is preferably repeated on a provider-by-provider basis for each procedure or service performed by health-care providers in the network.

Figure 11:
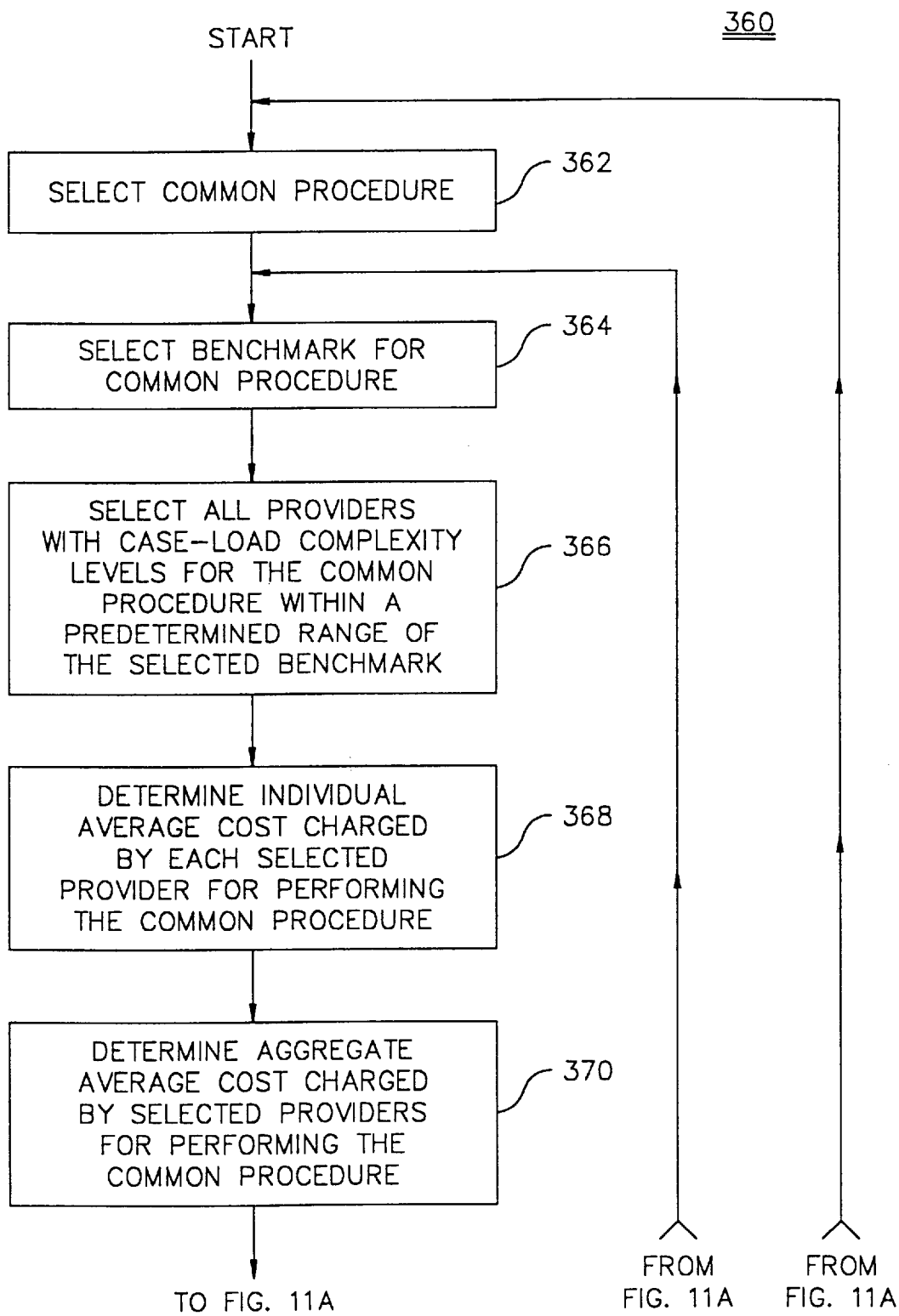
FIGS. 11 and 11A are a flow diagram showing the operation of a system for assessing the cost-efficiency of individual health-care providers within a group of health-care providers in accordance with a preferred embodiment of the present invention.
Figure 11A:
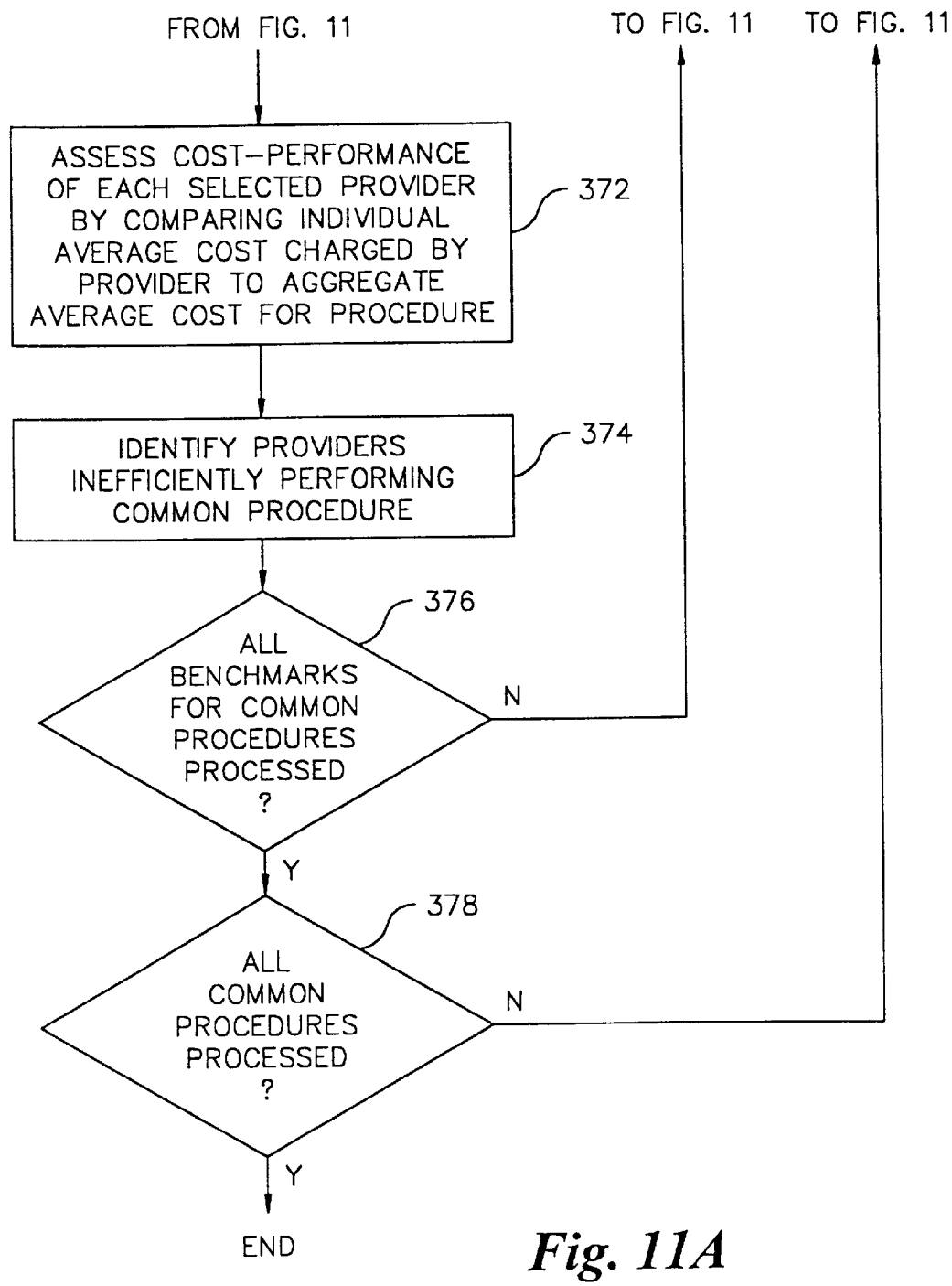

Referring now to FIGS. 11 and 11A, there is shown a flow diagram illustrating the operation of main step 360 and showing a system for assessing the cost-efficiency of individual health-care providers within a group of health-care providers in accordance with a preferred embodiment of the present invention. In step 362, a common procedure or service performed by multiple health-care providers in the network for patients is selected for analysis. When sub-system 300 is used in conjunction with the budget monitoring sub-system (steps 210–240) of system 200, the common procedure or service may correspond, for example, to the procedure typically used for treating the condition selected in step 210. In step 364, one of the severity comparison benchmarks (from step 328) associated with the selected procedure is selected for analysis. In step 366, all health-care providers in the network with case load complexity levels for the common procedure that are within a predetermined range of the selected benchmark are identified. In step 368, an average cost charged for performing the selected procedure is determined for each health-care provider that was identified in step 366. More particularly, for each health-care provider identified in step 366, the costs charged by the health-care provider for performing the selected procedure are extracted from the claim records stored in database 50 and then averaged. In step 370, an aggregate average cost charged for performing the selected procedure is determined based on each health-care provider that was identified in step 366. More particularly, in step 370, the costs charged for performing the selected procedure by all health-care providers across the network that were identified in step 366 are extracted from the claim records stored in database 50, added together on an aggregate basis, and then averaged. In step 372, a cost-efficiency performance level for each health-care provider that was identified in step 366 is determined by comparing the individual average cost charged by the health-care provider for performing the selected procedure (determined in step 368) with the aggregate average cost charged for performing the selected procedure across the network (determined in step 370). In a preferred embodiment, the selected health-care provider will be classified as having an "efficient" cost-efficiency performance level so long as the provider's individual average cost charged for the selected procedure is within a predetermined percentage of the aggregate average cost charged across the network for the procedure; otherwise, the selected provider will be classified as having an "inefficient" cost-performance level and will be flagged for review by workstation 90. As shown by blocks 376 and 378, the process of assessing the cost-performance levels of the health-care providers in the network may be repeated for each severity comparison benchmark associated with the selected procedure, and then on a procedure-by-procedure basis for each procedure or service performed by health-care providers in the network.

Since severity comparison benchmarks are used in main step 360 in assessing the cost-efficiency performance levels of the individual health-care providers in the network, the present invention insures that health-care providers that routinely handle more complicated cases are compared from a cost standpoint only against like health-care providers that also routinely handle more complicated cases, and that health-care providers that routinely handle less complicated cases are only compared from a cost standpoint against like health-care providers that also routinely handle less complicated cases.

The present invention may be embodied in other specific forms without departing from the spirit or essential attributes of the invention. Accordingly, reference should be made to the appended claims, rather than the foregoing specification, as indicating the scope of the invention.

What is claimed is:

1. An apparatus for objectively monitoring the performance of a group of health-care providers, comprising:

(A) a database storage means for storing in-patient payment claim records representative of in-patient health-care services performed for patients by health-care providers within said group of health-care providers and out-patient payment claim records representative of out-patient health-care services performed for said patients by health-care providers within said group of health-care providers;

(B) episode building means, coupled to said database storage means, for building a plurality of sickness episode data records from said in-patient payment claim records and said out-patient payment claim records;

(C) severity adjustment means, coupled to said episode building means, for performing an objective severity adjustment analysis on said plurality of sickness episode data records to form a plurality of severity-adjusted sickness episode data records; and (D) a computer workstation, coupled to said database storage means, said computer workstation including:

(i) cost-efficiency performance assessment means, responsive to said plurality of severity adjusted sickness episode data records, for objectively determining a cost-efficiency performance level for each individual health-care provider within said group of health-care providers;

(ii) qualitative-performance assessment means, responsive to said in-patient payment claim records and said out-patient payment claim records, for objectively measuring a qualitative performance level of said group of health-care providers as a whole; and (iii) budget monitoring means for determining a total illness cost value representing costs incurred by said group of health-care providers as a whole for treating a selected condition and comparing said total illness cost value to a predetermined budgeted illness cost value associated with said selected condition.

2. The apparatus of claim 1, wherein each of said in-patient payment claim records and each of said out-patient payment claim records includes a provider identification code field, a patient identification code field, a service provided code field and a date of service field, said apparatus further comprising:

(E) individual payment claim record auditing means, coupled to said computer workstation, for analyzing said in-patient payment claim records and said out-patient payment claim records on a record-by-record basis and identifying predetermined sentinel events from said in-patient and said out-patient payment claim records.

3. The apparatus of claim 2, wherein said predetermined sentinel events represent unapproved medical services performed by health-care providers within said group of health-care providers.

4. The apparatus of claim 1, wherein said cost-efficiency performance assessment means determines a cost-efficiency performance level associated with treating said selected condition for each individual health-care provider within said group of health-care providers when said budget monitoring means determines that said total illness cost value for treating said selected condition exceeds said predetermined budgeted illness cost value.

5. The apparatus of claim 4, wherein said episode building means builds said plurality of sickness episode data records by combining information from said in-patient and out-patient payment claim records, each sickness episode data record within said plurality of sickness episode data records corresponding to an individual sickness episode for which health-care services were performed for one of said patients by at least one health-care provider from said group of health-care providers.

6. The apparatus of claim 5, wherein said severity assessment means performs objective severity assessments on a group of sickness episode data records and assigns, in response to said objective severity assessments, an episode severity score to each sickness episode data record within said group of sickness episode data records.

7. The apparatus of claim 6, wherein said cost-efficiency performance assessment means is coupled to means for objectively determining case load complexity levels for health-care providers within said group of health-care providers from said episode severity scores, and said cost-efficiency performance levels are determined in accordance with said case load complexity levels.

8. The apparatus of claim 7, wherein each of said case load complexity levels is representative of patients that received a common procedure from one of said health-care providers within said group of health-care providers.

9. The apparatus of claim 5, wherein said individual sickness episode corresponds to a time period that begins when a patient begins to feel sick and ends when said patient is no longer sick.

10. The apparatus of claim 9, wherein said time period begins before any health-care services were performed for said patient by any health-care provider.

11. A computer-implemented method for objectively monitoring the performance of a group of health-care providers, comprising the steps of:

(A) storing in a database storage means in-patient payment claim records representative of in-patient health-care services performed for patients by health-care providers within said group of health-care providers and out-patient payment claim records representative of out-patient health-care services performed for said patients by health-care providers within said group of health-care providers;

(B) building a plurality of sickness episode data records from said in-patient payment claim records and said out-patient payment claim records;

(C) performing an objective severity adjustment analysis on said plurality of sickness episode data records to form a plurality of severity-adjusted sickness episode data records;

(D) objectively determining a cost-efficiency performance level for each individual health-care provider within said group of health-care providers from said plurality of severity-adjusted sickness episode data records;

(E) objectively measuring a qualitative performance level of said group of health-care providers as a whole; and (F) determining a total illness cost value representing costs incurred by said group of health-care providers as a whole for treating a selected condition and comparing said total illness cost value to a predetermined budgeted illness cost value associated with said selected condition.

12. The method of claim 11, wherein each of said in-patient payment claim records and each of said out-patient payment claim records includes a provider identification code field, a patient identification code field, a service provided code field and a date of service field, said method further comprising the step of:

(G) analyzing said in-patient payment claim records and said out-patient payment claim records on a record-by-record basis and identifying predetermined sentinel events from said in-patient and said out-patient payment claim records.

13. The method of claim 12, wherein said predetermined sentinel events represent unapproved medical services performed by health-care providers within said group of health-care providers.

14. The method of claim 11, wherein a cost-efficiency performance level associated with treating said selected condition for each individual health-care provider within said group of health-care providers is determined in step (D) when said total illness cost value for treating said selected condition exceeds said predetermined budgeted illness cost value.

15. The method of claim 14, wherein said plurality of sickness episode data records are built in step (B) by combining information from said in-patient and out-patient payment claim records, each sickness episode data record within said plurality of sickness episode data records corresponding to an individual sickness episode for which health-care services were performed for one of said patients by at least one health-care provider from said group of health-care providers.

16. The method of claim 15, wherein step (C) comprises the step of performing objective severity assessments on a group of sickness episode data records and assigning, in response to said objective severity assessments, an episode severity score to each sickness episode data record within said group of sickness episode data records.

17. The method of claim 16, further comprising the step of objectively determining case load complexity levels for health-care providers within said group of health-care providers from said episode severity scores, wherein said cost-efficiency performance levels are determined in step (D) in accordance with said case load complexity levels.

18. The method of claim 17, wherein each of said case load complexity levels is representative of patients that received a common procedure from one of said health-care providers within said group of health-care providers.

19. The method of claim 15, wherein said individual sickness episode corresponds to a time period that begins when a patient begins to feel sick and ends when said patient is no longer sick.

20. The method of claim 19, wherein said time period begins before any health-care services were performed for said patient by any health-care provider from said group of health-care providers.

21. An apparatus for objectively monitoring the performance of a group of health-care providers, comprising:
(A) a database storage means for storing in-patient payment claim records representative of in-patient health-care services performed for patients by health-care providers within said group of health-care providers and out-patient payment claim records representative of out-patient health-care services performed for said patients by health-care providers within said group of health-care providers;
(B) episode building means, coupled to said database storage means, for building a plurality of sickness episode data records from said in-patient payment claim records and said out-patient payment claim records;
(C) severity adjustment means, coupled to said episode building means, for performing an objective severity adjustment analysis on said plurality of sickness episode data records to form a plurality of severity-adjusted sickness episode data records; and
(D) a computer workstation, coupled to said database storage means, said computer workstation including:
(i) cost-efficiency performance assessment means, responsive to said plurality of severity adjusted sickness episode data records, for objectively determining a cost-efficiency performance level for each individual health-care provider within said group of health-care providers;
(ii) qualitative-performance assessment means, responsive to said in-patient payment claim records and said out-patient payment claim records, for objectively measuring a qualitative performance level of said group of health-care providers as a whole based on preventive-care services associated with a selected condition; and
(iii) budget monitoring means for determining a total illness cost value representing costs incurred by said group of health-care providers as a whole for treating a selected condition and comparing said total illness cost value to a predetermined budgeted illness cost value associated with a selected condition.

22. The apparatus of claim 21, wherein said qualitative-performance assessment means determines a qualitative-performance level associated with treating said selected condition for said group of health-care providers as a whole when said budget monitoring means determines that said total illness cost value for treating said selected condition exceeds said predetermined budgeted illness cost value.

23. The apparatus of claim 22, wherein said selected condition corresponds to breast cancer and said qualitative-performance level corresponds to a percentage of women treated by said group of health-care providers receiving mammograms.

24. The apparatus of claim 22, wherein said selected condition corresponds to diabetes and said qualitative-performance level corresponds to a percentage of diabetes patients treated by said group of health-care providers receiving eye examinations.

25. A computer-implemented method for objectively monitoring the performance of a group of health-care providers, comprising the steps of:
(A) storing in a database storage means in-patient payment claim records representative of in-patient health-care services performed for patients by health-care providers within said group of health-care providers and out-patient payment claim records representative of out-patient health-care services performed for said patients by health-care providers within said group of health-care providers;
(B) building a plurality of sickness episode data records from said in-patient payment claim records and said out-patient payment claim records;
(C) performing an objective severity adjustment analysis on said plurality of sickness episode data records to form a plurality of severity-adjusted sickness episode data records;
(D) objectively determining a cost-efficiency performance level for each individual health-care provider within said group of health-care providers from said plurality of severity-adjusted sickness episode data records;
(E) objectively measuring a qualitative performance level of said group of health-care providers as a whole based on preventive-care services associated with a selected condition; and
(F) determining a total illness cost value representing costs incurred by said group of health-care providers as a whole for treating a selected condition and comparing said total illness cost value to a predetermined budgeted illness cost value associated with said selected condition.

26. The method of claim 25, wherein a qualitative-performance level associated with treating said selected condition for said group of health-care providers as a whole is determined in step (E) when said total illness cost value for treating said selected condition exceeds said predetermined budgeted illness cost value.

27. The method of claim 26, wherein said selected condition corresponds to breast cancer and said qualitative-performance level corresponds to a percentage of women treated by said group of health-care providers receiving mammograms.

28. The method of claim 27, wherein said selected condition corresponds to diabetes and said qualitative-performance level corresponds to a percentage of diabetes patients treated by said group of health-care providers receiving eye examinations.

* * * * *